(12) United States Patent  (10) Patent No.: US 8,806,953 B2
Kim  (45) Date of Patent: Aug. 19, 2014

(54) BENDING TEST APPARATUS FOR FLEXIBLE DEVICE

(75) Inventor: Gi Heon Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 184 days.

(21) Appl. No.: 13/459,600

(22) Filed: Apr. 30, 2012

(65) Prior Publication Data

US 2012/0285257 A1    Nov. 15, 2012

(30) Foreign Application Priority Data

May 13, 2011    (KR) .................. 10-2011-0045251

(51) Int. Cl.
*G01N 3/20* (2006.01)
*G01M 5/00* (2006.01)

(52) U.S. Cl.
CPC . *G01N 3/20* (2013.01); *G01M 5/005* (2013.01)
USPC ............................. 73/849; 73/856; 310/49.01

(58) Field of Classification Search
CPC ......... G01N 3/20; G01N 27/04; G01N 27/00; G01N 27/041
USPC .................................................. 73/849, 853
See application file for complete search history.

(56) References Cited

U.S. PATENT DOCUMENTS

| 3,986,746 A * | 10/1976 | Chartier ........................ 294/116 |
| 7,882,748 B2 * | 2/2011 | Wen et al. ....................... 73/849 |
| 2002/0059834 A1 * | 5/2002 | Onoue ............................ 73/812 |
| 2003/0061885 A1 | 4/2003 | Auch et al. |

FOREIGN PATENT DOCUMENTS

KR    10-2011-0114256 A    10/2011

OTHER PUBLICATIONS

Jing-Yi Yan et al., "The stability of a-IGZO thin film transistors on plastic substrate with mechanical and illumination stress", IDW, 2009, pp. 1609-1612.

* cited by examiner

*Primary Examiner* — Lisa Caputo
*Assistant Examiner* — Roger Hernandez-Prewit
(74) *Attorney, Agent, or Firm* — Rabin & Berdo, P.C.

(57) ABSTRACT

Provided is a bending test apparatus for flexible substrate which may increase or maximize reliability. The bending test apparatus includes a table, a first electrode part fixing one side of a flexible substrate on the table, a guide rail disposed adjacent to the first electrode part, the guide rail extending from the one side of the flexible substrate to the other side, a slider moved along the guide rail, and a second electrode part connected to the slider, the second electrode part approaching or spacing the other side of the flexible substrate to/from the first electrode part.

6 Claims, 8 Drawing Sheets

BENDING TEST APPARATUS FOR FLEXIBLE DEVICE

CROSS-REFERENCE TO RELATED APPLICATIONS

This U.S. non-provisional patent application claims priority under 35 U.S.C. §119 of Korean Patent Application No. 10-2011-0045251, filed on May 13, 2011, the entire contents of which are hereby incorporated by reference.

BACKGROUND OF THE INVENTION

The embodiment of the inventive concept disclosed herein relates to a test apparatus, and more particularly, to a bending test apparatus for flexible device.

Since a display device manufactured on a glass substrate is not bent, the reliability with respect to an electrical stress is mainly assessed. However, since a flexible device such as a display device manufactured on a flexible substrate is bent, a mechanical stress in addition to the electrical stress may be applied. Thus, it is needed to measure the reliability of a thin film deposited on the substrate or the flexible device with respect to the mechanical stress.

SUMMARY OF THE INVENTION

The embodiment of the inventive concept provides a bending test apparatus for flexible substrate which may increase or maximize reliability.

Embodiments of the inventive concept provide bending test apparatuses including: a table; a first electrode part fixing one side of a flexible substrate on the table; a guide rail disposed adjacent to the first electrode part, the guide rail extending from the one side of the flexible substrate to the other side; a slider moved along the guide rail; and a second electrode part connected to the slider, the second electrode part approaching or spacing the other side of the flexible substrate to/from the first electrode part.

In some embodiments, the first and second electrode parts may be clamps having grooves in which the one side and the other side of the flexible substrate are inserted, respectively. The clamps may include a lower electrode bar and an upper electrode bar which are respectively engaged with upper and lower portions of the flexible substrate. The clamps may further include guide pins for adjusting sizes of the grooves between the lower electrode bar and the upper electrode bar. The clamps may further include springs through which the guide pins pass between the lower electrode bar and the upper electrode bar, the springs spacing the lower clamp from the upper electrode bar. The clamps may further include electrode shafts coupled to both sides of the lower electrode bar. The bending test apparatuses may further include first elbows fixing the first electrode part on the table to support the electrode shafts of the first electrode part. The bending test apparatus may further include: a movement shaft connected between the slider and the second electrode part, the movement shaft extending in a direction parallel to that of the first electrode part; and second elbows supporting the electrode shafts of the second electrode part on the movement shaft.

In other embodiments, the bending test apparatuses may further include: a driving part moving the slider; and a control part outputting a control signal for controlling the driving, the control part performing an electrical performance test by bending or unfolding the flexible substrate between the first electrode part and the second electrode part.

In still other embodiments, the bending test apparatuses may further include a housing covering an upper side of the table.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Preferred embodiments of the inventive concept will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explaining a specific exemplary embodiment while not limiting the inventive concept. The terms of a singular form may include plural forms unless specifically mentioned. The meaning of 'comprises' and/or 'comprising' specifies an element, a process, an operation and/or a device but does not exclude other elements, processes, operations and/or devices. Since preferred embodiments are provided below, the order of the reference numerals given in the description is not limited thereto. In the specification, it will be understood that when a layer (or film) is referred to as being 'on' another layer or substrate, it can be directly on the other layer or substrate, or intervening layers may also be present.

Figure 1:
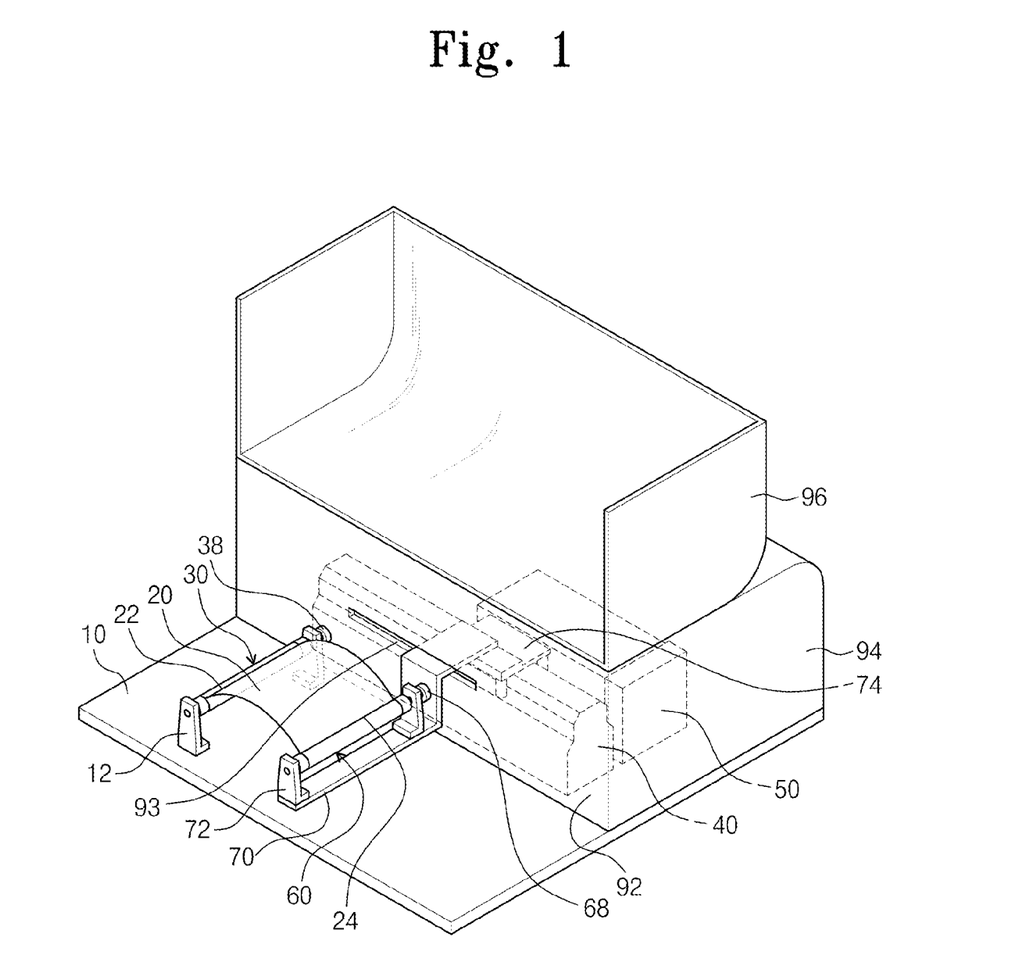
FIG. 1 is a perspective view of a bending test apparatus for flexible substrate according to an embodiment of the inventive concept.
Figure 2:
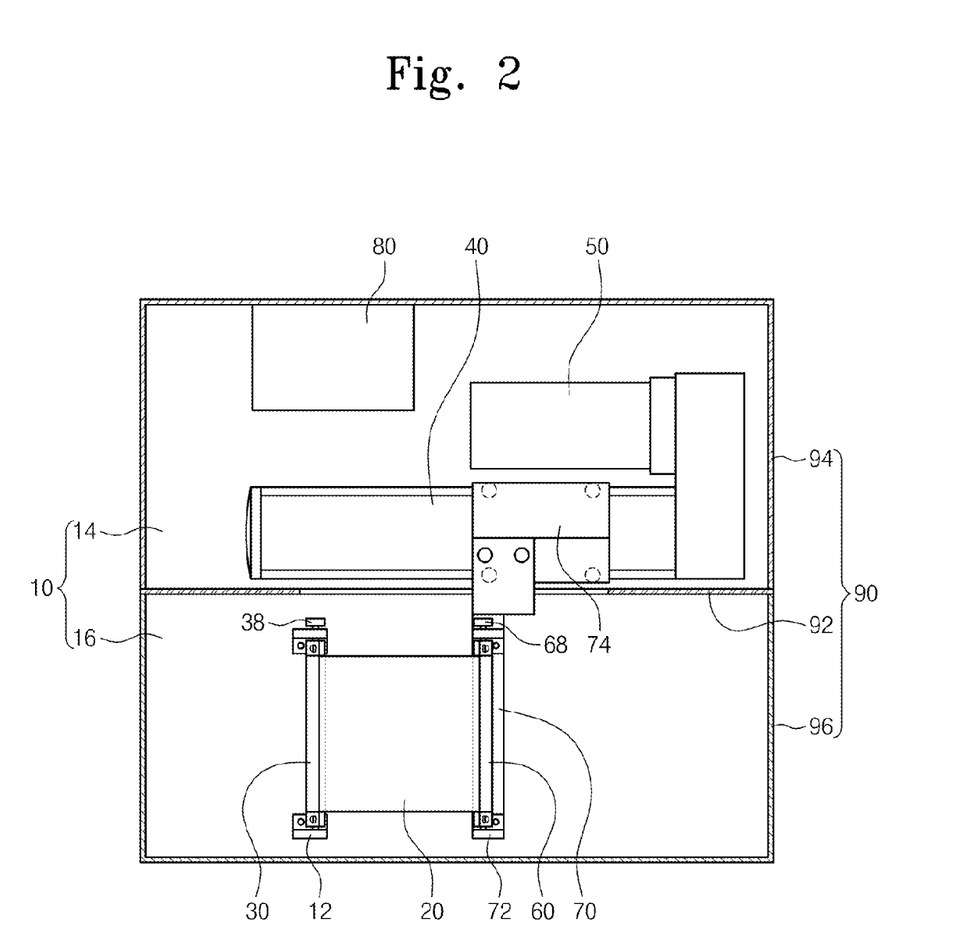
FIGS. 2 and 3 are plan and side views illustrating the bending test apparatus for flexible substrate of FIG. 1, respectively.
Figure 3:
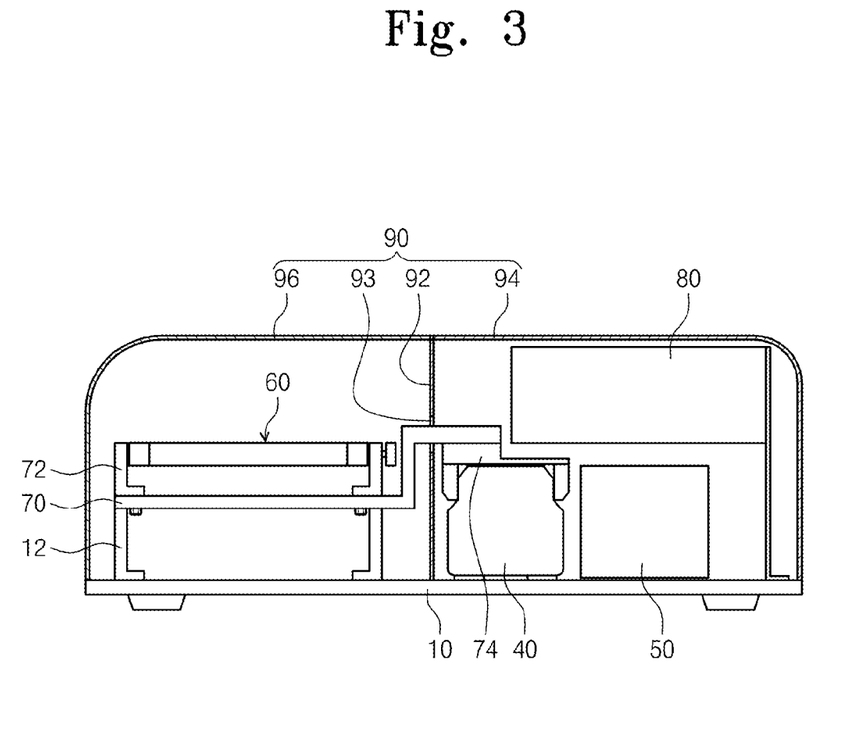

FIG. 1 is a perspective view of a bending test apparatus for flexible substrate according to an embodiment of the inventive concept. FIGS. 2 and 3 are plan and side views illustrating the bending test apparatus for flexible substrate of FIG. 1, respectively.

Referring to FIGS. 1 to 3, a test apparatus according to the embodiment of the inventive concept may include a first electrode part 30 fixed to one side 22 of a flexible substrate 20 above a table 10 and a second electrode part 60 moving the other side 24 of the flexible substrate 20 fixed to the first electrode part 30. The first electrode part 30 may be fixed to first elbows 12 coupled to the table 10. The second electrode part 60 may be horizontally moved by a slider 74 and a movement shaft 70. The flexible substrate 20 may be bent by approaching the first and second electrode parts 30 and 60. The first and second electrode parts 30 and 60 may be electrically connected to the flexible substrate 20. A control part 80 may outputs a control signal for controlling a driving part 50 to test electrical performance due to the bending of the flexible substrate 20. The flexible substrate 20 may be quantitatively bent or unfolded according to the movement of the second electrode part 60.

Thus, the bending test apparatus for flexible substrate 20 according to an embodiment of the inventive concept may improve or maximize test reliability.

The table 10 may include a control region 14 and a test region for flexible substrate 20 which are separated by a partition 92 of a housing 90. The housing 90 may surround an upper side of the table 10. The housing 90 may include a first housing 94 covering the control region 14, a second housing 96 covering the test region 16, and the partition 92 between the second housing 96 and the first housing 94. The first and second housings 94 and 96 may be independently opened or closed. The second housing 96 may be fluidly opened when the flexible substrate 20 is loaded/unloaded. The partition 92 may include an opening 93 through which the movement shaft 70 passes between the second electrode part 60 and a guide rail 40. The opening 93 may be defined in the same direction as that of the guide rail 40.

The guide rail 40, the slider 74, the driving part 50, and the control part 80 may be disposed in the control region 14. The guide rail 40 may extend from the one side 22 of the flexible substrate 20 to the other side 24. The guide rail 40 may be disposed adjacent to the first electrode part 30 on the table 10. The guide rail 40 may extend from the one side 22 of the flexible substrate 20 to the other side 24. The slider 74 may be moved along the guide rail 40. The driving part 50 may generate power for moving the slider 74. Although not shown, the driving part 50 may include a step motor for generating rotation power according to the control signal of the control part 80 and a bevel gear and/or crank for linearly moving the slider 74 along the guide rail 40 by the rotation power of the step motor. The control part 80 may be electrically connected to the first and second electrode parts 30 and 60 by first and second cables (not shown).

The first and second electrode parts 30 and 60 may be disposed in the test region 16. The first electrode part 30 may be fixed to the table 10. The first elbows 12 may be fixed to the table 10. The first elbows 12 may fix the first electrode part 30 to the table 10. The second electrode part 60 may be fixed to the movement shaft 70 by second elbows 72. The movement shaft 70 may be coupled to the slider 74 disposed in the control region 14. The movement shaft 70 may pass through the opening 93 of the partition 92 to extend in a direction parallel to that of the first electrode part 30. The second electrode part 60 may be fixed to the movement shaft 70. The second elbows 72 may support the second electrode part 60 on the movement shaft 70. The second electrode part 60 may be moved by the movement shaft 70 and the slider 74.

Figure 4:
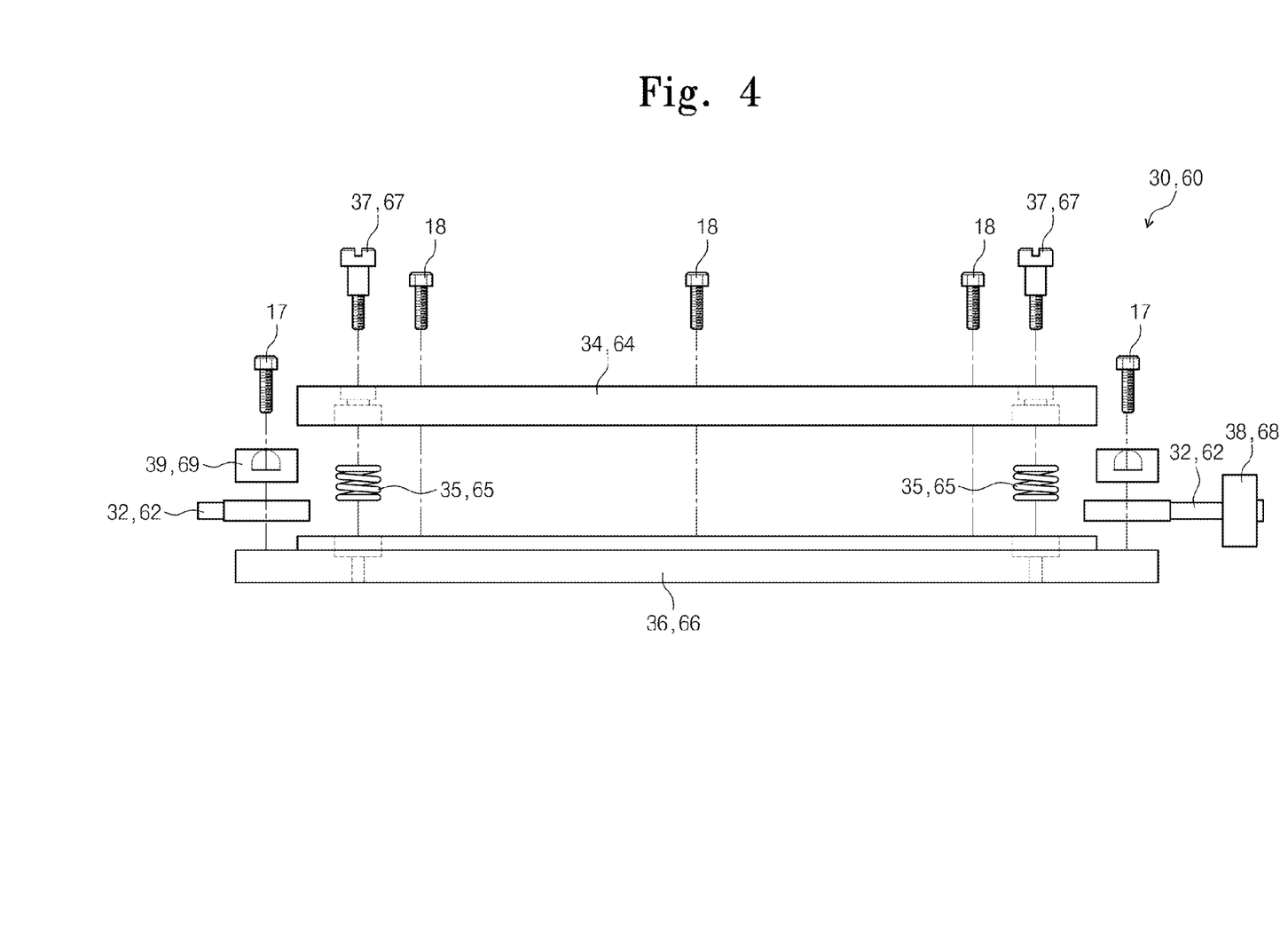
FIG. 4 is an exploded view of first and second electrode parts.
Figure 5:
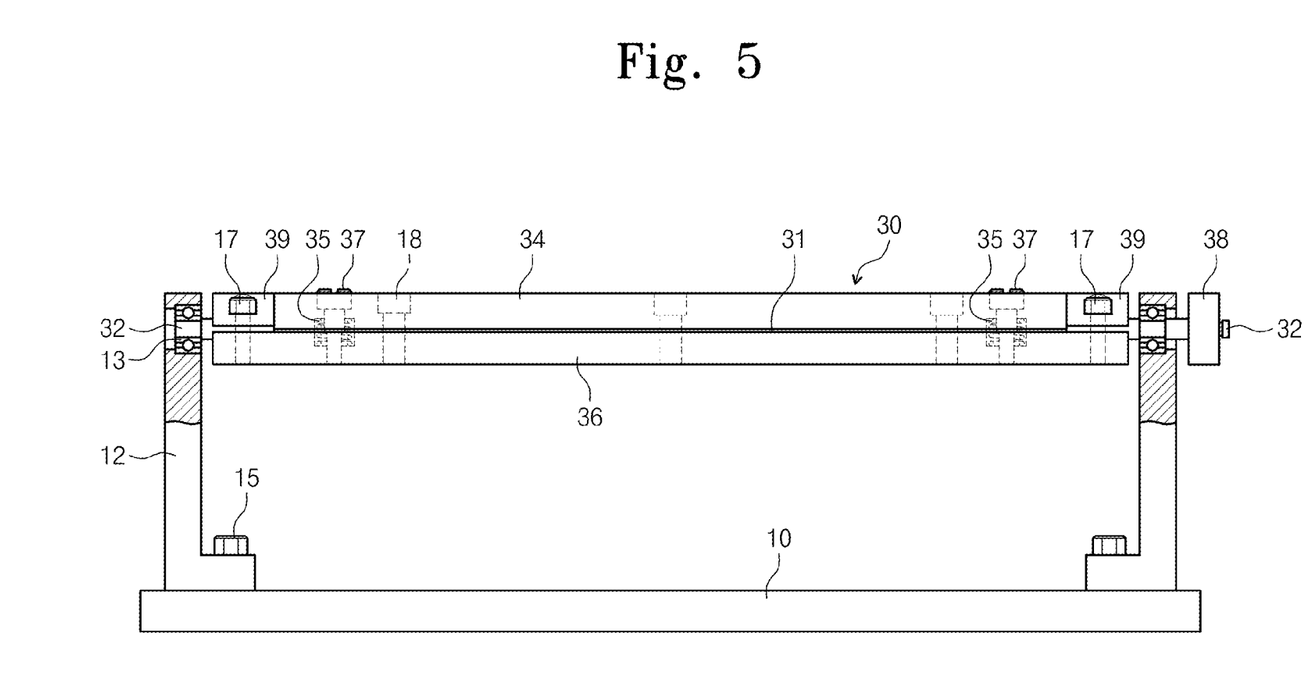
FIGS. 5 and 6 are cross-sectional and longitudinal section views of the first electrode part, respectively.
Figure 6:
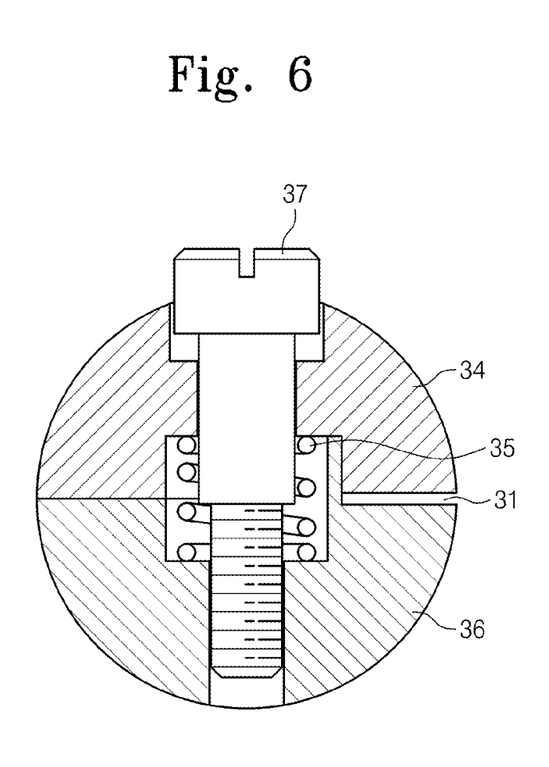
Figure 7:
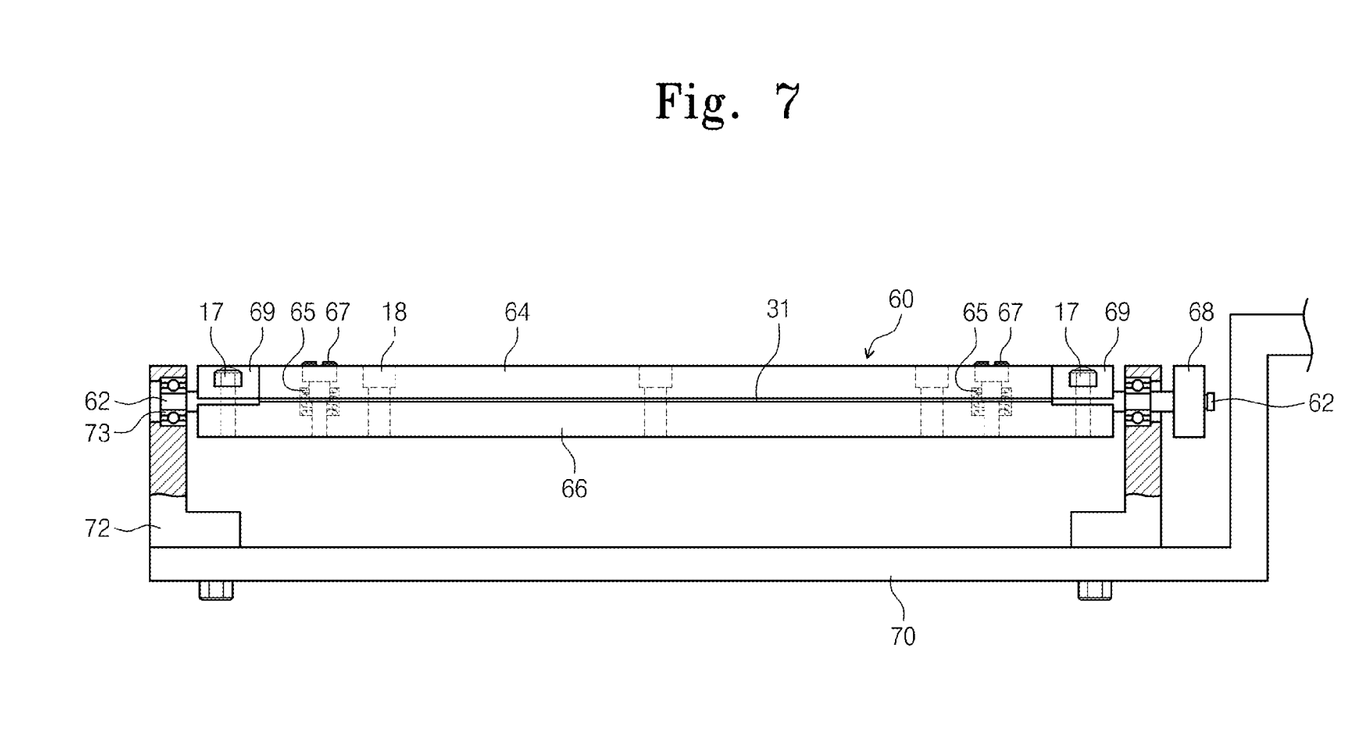
FIGS. 7 and 8 are cross-sectional and longitudinal section views of a second electrode part, respectively.
Figure 8:
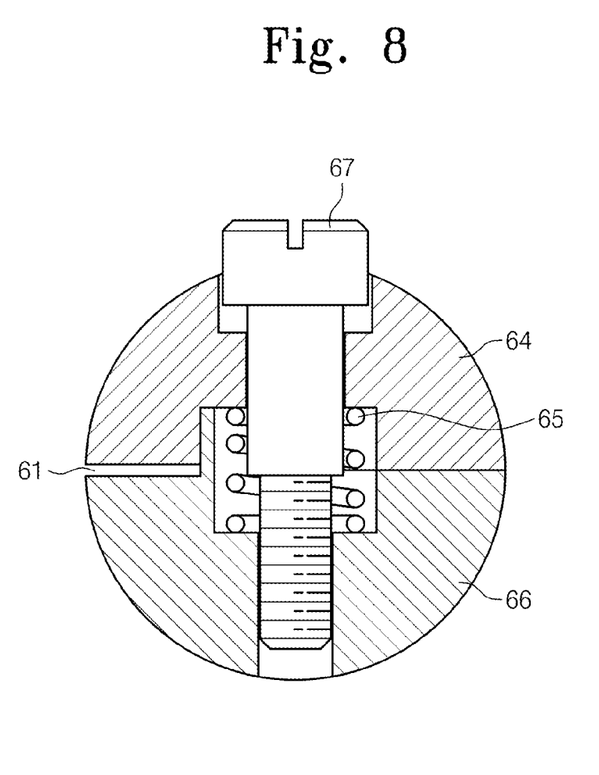

FIG. 4 is an exploded view of the first and second electrode parts. FIGS. 5 and 6 are cross-sectional and longitudinal section views of the first electrode part, respectively. FIGS. 7 and 8 are cross-sectional and longitudinal section views of a second electrode part, respectively.

Referring to FIGS. 1 to 6, the first electrode part 30 may be a first clamp having a first groove 31 in which the one side 22 of the flexible substrate 20 is inserted. The first electrode part 30 may include a first lower electrode bar 36 and a first upper electrode bar 34. The first lower electrode bar 36 and the first upper electrode bar 34 may be engaged to fix the one side 22 of the flexible substrate 20. The first lower electrode bar 36 may be connected between first electrode shafts 32. The first electrode shafts 32 may be supported by the first elbows 12. The first electrode shafts 32 may be fixed to both sides of the first lower electrode bar 36 by first caps 39 and second bolts 17. When a distance between the first and second electrode parts 30 and 60 is changed, the first electrode shafts 32 may be rotated on the first elbows 12 by bending and/or unfolding the flexible substrate 20. A first bearing 13 may help the rotation of the first electrode shaft 32. The first bearing 13 may reduce friction between the first electrode shaft 32 and the first elbows 12. The first elbows 12 may be fixed to the table 10 by first bolts 15. A first terminal holder 38 may be coupled to an end of the first electrode shaft 32 adjacent to the partition 92. The first electrode shafts 32 may be formed of a conductive metal having a low resistance. A first cable (not shown) may be connected from the first terminal holder 38 to the control part 80. The first upper electrode bar 34 may be coupled and engaged on the first lower electrode bar 36. The first upper electrode bar 34 may be coupled to the first lower electrode bar 36 by third bolts 18. A first groove 31 may correspond to a gap between the first upper electrode bar 34 and the first lower electrode bar 36. Here, the flexible substrate 20 may be introduced through the gap. The first groove 31 may have a size of about 1 mm to about 3 mm. First guide pins 37 may adjust the size of the first groove 31. The first guide pins 37 may be inserted into nut holds (not shown) of the first upper and lower electrode bars 34 and 36. The first guide pins 37 may adjust the gap between the first upper and lower electrode bars 34 and 36. The first springs 35 may space the first lower and upper electrode bars 36 and 34 from each other. The first guide pins 37 may pass through the insides of the first springs 35, respectively. The first guide pins 37 may fix the one side 22 of the flexible substrate 20 introduced into the first upper and lower electrode bars 34 and 36 through the first groove 31. Each of the first upper and lower electrode bars 34 and 36 may be formed of at least one of copper, aluminum, and/or a combination thereof. The first upper and lower electrode bars 34 and 36 may electrically contact the conductive material of the flexible substrate 20.

Referring to FIGS. 1 to 8, the second electrode part 60 may fix the other side 24 of the flexible substrate 20. The second electrode part 60 may be electrically connected to the other side 24 of the flexible substrate 20. The second electrode part 60 may have a structure similar to that of the first electrode part 30 and thus be disposed symmetric to the first electrode part 30. The second electrode part 60 may be a second clamp having a second groove 61 in which the other side 24 of the flexible substrate 20 is inserted. The second electrode part 60 may include second electrode shafts 62 supported by the second elbows 72 of the movement shaft 70, a second lower electrode bar 66 connected between the second electrode shafts 62, and a second upper electrode bar 64 coupled to the second lower electrode bar 66 to fix the other side 24 of the flexible substrate 20. The second electrode shafts 62 may be fixed to both sides of the second lower electrode bar 66 by second caps 69 and the second bolts 17. The second electrode shafts 62 may be rotated by bending and/or unfolding the flexible substrate 20. Second bearings 73 may reduce friction between the second electrode shafts 62 and the second elbows 72. A second terminal holder 68 may be coupled to an end of the second electrode shaft 62 adjacent to the partition 92. The second electrode shafts 62 may be formed of a conductive metal having a low resistance. A second cable (not shown) may be connected from the second terminal holder 68 to the control part 80. The second upper electrode bar 64 may be engaged and coupled on the second lower electrode bar 66 by the third bolts 18. The other side 24 of the flexible substrate 20 may be introduced into a second groove 61. Second guide pins 67 may adjust a size of the second groove 61. A second spring 65 may space the second lower and upper electrode bars 66 and 64 from each other. The second guide pins 67 may pass through the second spring 65. Second guide pins 77 may be inserted into nut holds of the second upper and lower electrode bars 64 and 66. The second guide pins 67 may fix the other side 24 of the flexible substrate 20 introduced into the second upper and lower electrode bars 64 and 66 through the second groove 61. Each of the second upper electrode bar 64 and the second lower electrode bar 66 may be formed of at least one of copper, aluminum, and/or a combination thereof. The second electrode part 60 may approach or away from the first electrode part 30 according to the control signal of the control part 80. The flexible substrate 20 may be quantitatively bent or unfolded according to the movement of the second electrode part 60.

Thus, the bending test apparatus for flexible substrate 20 according to an embodiment of the inventive concept may improve or maximize test reliability of the flexible substrate 20.

As described above, according to the embodiment of the inventive concept, the first and second electrode parts may be fixed to the one side and the other side of the flexible substrate having various sizes, respectively. The first electrode part may be fixed to the first elbows on the table. The second electrode part may be connected to the slider moved along the guide rail. The slider may be moved along the guide rail by the power of the driving part. The flexible substrate may be quantitatively bent and/or unfolded according to the movement of the second electrode part. Thus, the bending test apparatus for flexible substrate according to the embodiment of the inventive concept may improve or maximize the test reliability.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A bending test apparatus comprising:
    a table;
    a first electrode part fixing one side of a flexible substrate on the table;
    a guide rail disposed adjacent to the first electrode part, the guide rail extending from the one side of the flexible substrate to other side of the flexible substrate;
    a slider moved along the guide rail; and
    a second electrode part connected to the slider, the second electrode part approaching or spacing the other side of the flexible substrate to/from the first electrode part,
    wherein:
    the first and second electrode parts are clamps having grooves in which the one side and the other side of the flexible substrate are inserted, respectively;
    the clamps comprise a lower electrode bar and an upper electrode bar which are respectively engaged with upper and lower portions of the flexible substrate;
    the clamps further comprise electrode shafts coupled to both sides of the lower electrode bar; and
    the bending test apparatus further comprises:
    a movement shaft connected between the slider and the second electrode part, the movement shaft extending in a direction parallel to that of the first electrode part; and
    second elbows supporting the electrode shafts of the second electrode part on the movement shaft.

2. The bending test apparatus of claim 1, wherein the clamps further comprise guide pins for adjusting sizes of the grooves between the lower electrode bar and the upper electrode bar.

3. The bending test apparatus of claim 2, wherein the clamps further comprise springs through which the guide pins pass between the lower electrode bar and the upper electrode bar, the springs spacing the lower clamp from the upper electrode bar.

4. The bending test apparatus of claim 1, further comprising first elbows fixing the first electrode part on the table to support the electrode shafts of the first electrode part.

5. The bending test apparatus of claim 1, further comprising:
    a driving part moving the slider; and
    a control part outputting a control signal for controlling the driving, the control part performing an electrical performance test by bending or unfolding the flexible substrate between the first electrode part and the second electrode part.

6. The bending test apparatus of claim 1, further comprising a housing covering an upper side of the table.

* * * * *